US006234984B1

(12) United States Patent
Kelly et al.

(10) Patent No.: US 6,234,984 B1
(45) Date of Patent: *May 22, 2001

(54) CHEST COMPRESSION APPARATUS FOR CARDIAC ARREST

(75) Inventors: Kevin A. Kelly, Galloway; Thomas E. Lach; Ralph D. Lach, both of Columbus; Arthur W. Handshy, Worthington, all of OH (US)

(73) Assignee: Deca-Medics, Inc., Hilliard, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/059,497

(22) Filed: Apr. 13, 1998

Related U.S. Application Data

(63) Continuation of application No. 08/573,465, filed on Dec. 15, 1995, now Pat. No. 5,738,637.

(51) Int. Cl.[7] .................................................. A61H 31/00
(52) U.S. Cl. ................................................ 601/41; 601/44
(58) Field of Search ................................ 601/41, 44, 134, 601/135, 133; 600/16; 482/19, 131

(56) References Cited

U.S. PATENT DOCUMENTS

| 651,962 | 6/1900 | Boghean . |
|---|---|---|
| 1,399,034 | 12/1921 | Taplin . |
| 2,071,215 | 2/1937 | Petersen . |
| 2,699,163 | 1/1955 | Engstrom . |
| 2,754,817 | 7/1956 | Nemeth . |
| 2,780,222 | 2/1957 | Polzin et al. . |
| 2,853,998 | 9/1958 | Emerson . |
| 2,899,955 | 8/1959 | Huxley . |
| 3,042,024 | 7/1962 | Mendelson . |
| 3,120,228 | 2/1964 | Huxley . |
| 3,368,550 | 2/1968 | Glascock . |
| 3,374,783 | 3/1968 | Hurvitz . |
| 3,425,409 | 2/1969 | Isaacson et al. . |
| 3,461,860 | 8/1969 | Barkalow . |
| 3,481,327 | 12/1969 | Drennen . |
| 3,491,751 | 1/1970 | Wolfing . |
| 3,503,388 | 3/1970 | Cook . |
| 3,777,744 | 12/1973 | Fryfogle et al. . |
| 3,782,371 | 1/1974 | Derouineau . |
| 4,060,079 | 11/1977 | Reinhold, Jr. . |
| 4,326,507 | 4/1982 | Barkalow . |
| 4,338,924 | 7/1982 | Bloom . |
| 4,397,306 | 8/1983 | Weisfeldt et al. . |
| 4,424,806 | 1/1984 | Newman et al. . |
| 4,770,164 | 9/1988 | Lach et al. . |
| 4,928,674 | 5/1990 | Halperin et al. . |
| 5,167,602 | 12/1992 | Lehktman . |
| 5,287,846 | 2/1994 | Capjon et al. . |
| 5,295,481 | 3/1994 | Geeham . |
| 5,407,418 | 4/1995 | Szpur . |
| 5,484,391 | 1/1996 | Buckman, Jr. et al. . |
| 5,490,820 | 2/1996 | Schock et al. . |
| 5,738,637 | * 4/1998 | Kelly et al. ............................ 601/41 |

FOREIGN PATENT DOCUMENTS 642118   1/1936   (GB) .

* cited by examiner

Primary Examiner—Michael A. Brown
Assistant Examiner—Benjamin K. Koo
(74) Attorney, Agent, or Firm—Eugene F. Friedman

(57) ABSTRACT

The invention is an apparatus for increasing intrathoracic pressure for resuscitating cardiac arrest patients. The apparatus comprises a flexible, substantially inelastic belt wrapped around the patient's chest and attached to a force converter. The force converter converts a downwardly directed force into a chestward resultant, which depresses the sternum, and two belt tightening resultants. The force converter comprises a pair of arm assemblies, each having a pair of spaced arms, which are pivotably mounted to a base. The base is positioned near the patient's sternum and the ends of the belt attach to one end of each arm assembly. The opposite, handle ends of the arm assemblies are depressed toward the chest causing tightening of the belt and compression of the chest cavity.

21 Claims, 10 Drawing Sheets

INVENTION OF ANOTHER

CHEST COMPRESSION APPARATUS FOR CARDIAC ARREST

The present application is a continuation of U.S. patent application Ser. No. 08/573,465 filed Dec. 15, 1995, and issued as U.S. Pat. No. 5,738,637 on Apr. 14, 1998.

TECHNICAL FIELD

This invention relates broadly to the field of medical devices and more specifically to an apparatus for increasing the blood flow by compressing the chest cavity of a person suffering from cardiac arrest.

BACKGROUND ART

During cardiac arrest, it is desirable to generate blood flow by external means in order to maintain brain and heart viability. Traditionally, the external means of generating blood flow has been manual cardiopulmonary resuscitation (CPR). Using CPR, the rescuer tilts the patient's head back, lifts the chin to clear and straighten the airway, and depresses the sternum 1½ to 2 inches 15 times (at a rate of 80 to 100 depressions per minute), after which the rescuer gives the patient 2 full breaths. This 15 depressions and 2 breaths is repeated cyclically.

Currently, the CPR research community believes that blood flow produced by external means can be explained by one, or a combination of two, theoretical mechanisms: the "cardiac pump" mechanism and the "thoracic pump" mechanism.

According to the cardiac pump mechanism, blood flow caused by external means is due to direct mechanical compression of the heart. During compression, blood is squeezed out of the heart chambers, and during release of the compression (relaxation) blood flows into the heart chambers. Backflow of the blood is prevented by the valving of the heart and vessels.

According to the thoracic pump mechanism, blood is pumped by external means as a result of the cyclical increase and decrease of intrathoracic pressure. During compression, the intrathoracic pressure rises, which causes blood to be forced out of the blood vessels and organs located in the thorax, and the blood flows into the peripheral tissues. During release, blood flows back into the thorax via the normal venous return. In this method, backflow is prevented by the valving of the veins.

Most researchers believe that both mechanisms are active to some degree However, the methods presently in use, and the devices currently in use, for promoting blood flow by the application of an external force are directed toward only one of the two mechanisms. In order to maximize blood flow, a device which takes advantage of both mechanisms is needed.

A variety of devices have been developed to increase blood and/or air flow in the chest cavity of a cardiac arrest patient.

U.S. Pat. No. 2,071,215 to Petersen shows a piston and cylinder arrangement attached to two ends of a girdle which encircles a patient's chest. The expansion or compression of a fluid in the piston and cylinder combination tightens and loosens the girdle to ventilate the lungs. This device is large and heavy, and is dependent upon a compressed fluid for driving power.

U.S. Pat. No. 3,425,409 to Isaacson et al. discloses an apparatus for compressing the sternum by a downward force generated by a piston. A belt is placed around the chest in order to minimize bodily damage, and air is applied to the air passages of the patient.

U.S. Pat. No. 5,287,846 to Capjon et al. shows an upper frame that rests on a patient, whose back rests on a lower frame. Retractable straps extend from the upper frame and attach to the lower frame. A hydraulic cylinder in the upper frame presses downwardly on the chest.

Barkalow, in U.S. Pat. No. 3,461,860, discloses a device using a pneumatic plunger to mechanically compress the sternum a predetermined distance. A mechanical ventilator was added to this device in U.S. Pat. No. 4,326,507 to insure proper ventilation and increase the volume of the chest. This device was limited in its success due to complexity which requires trained personnel to use it.

A similar device was disclosed in U.S. Pat. No. 4,060,079 to Reinhold, This device is merely a similar portable unit.

Bloom, in U.S. Pat. No. 4,338,924, shows a sternum compression device using an air cylinder to depress the chest of the cardiac arrest patient. This device, like many others using a chest compression design, is large and heavy.

Newman et al., in U.S. Pat. No. 4,424,806, show a pneumatic vest for generating a rise in thoracic pressure. This vest uses the "thoracic pump" concept of exerting greater force over a larger area under the assumption that if more major organs could be compressed and released, greater blood flow would occur. By releasing the compression force, the chest would return to its normal size and draw blood back into the major organs. Positive blood flow would occur due to the one-way valves in the vascular network. The Newman device is not readily portable, in addition to having substantial complexity. In U.S. Pat. No. 4,928,674, Halperin et al. disclose a similar vest which is similarly not portable.

Lach et al., in U.S. Pat. No. 4,770,164, disclose a circumferential band and take-up reel used to generate a rise in thoracic pressure. Although either manually or mechanically driven, this apparatus requires the use of a backboard for guiding the band around the chest.

The use of bands or belts to generate a rise in intrathoracic compression for the purpose of assisting respiratory ailments is disclosed in U.S. Pat. No. 651,962 to Boghean. This device is for periodic loosening and tightening of the band around a patient's chest for treating respiratory disease by regulating periods of breathing as well as the size or depth of breath.

In U.S. Pat. No. 3,777,744, Fryfogle et al. disclose a breathing aid consisting of a belt and a handle which tightens the belt for expelling excessive residual air in the lungs.

Other devices known to the Applicants using circumferential bands for generating a compression force on the abdomen and lower chest to assist in compression of lungs for respiratory purposes include U.S. Pat. No. 2,899,955 to Huxley, U.S. Pat. No. 3,368,581 to Glascock and U.S. Pat. No. 2,754,817 to Nemeth. Furthermore, the use of inflatable bladders positioned around either the chest or the abdomen have been disclosed in U.S. Pat. No. 3,481,327 to Drennen, U.S. Pat. No. 3,120,228 to Huxley, U.S. Pat. No. 3,042,024 to Mendelson, U.S. Pat. No. 2,853,998 to Emerson, U.S. Pat. No. 2,780,222 to Polzin, U.S. Pat. No. 2,071,215 to Petersen, U.S. Pat. No. 4,424,806 to Newman and U.S. Pat. No. 4,928,674 to Halperin.

U.S. Pat. No. 2,699,163 to Engstrbm, shows a respirator device for ventilating a patient's lungs.

U.S. Pat. No. 5,295,481 to Geeham shows a chest compression device comprising a T-shaped mechanical chest compression apparatus with a suction cup. The central shaft attached to the cup may be compressed beyond the lips of the cup and bruise or otherwise injure the patient due to the concentration of force on the patient by the shaft tip.

U.S. Pat. Nos. 4,397,306 to Weisfeldt et al. and 1,399,034 to Taplin show large mechanical devices for compressing the chest of a cardiac arrest patient.

Szpur, in U.S. Pat. No. 5,407,418, discloses a power-driven, pulsating compressor apparatus for stimulating blood flow within vessels of a person's foot or hand. The device periodically applies a concentrated force against a localized region of the foot or hand.

In spite of the prior art, the need still exists for a device which effectively increases the flow of blood in the organs of a cardiac arrest patient. This device should be truly portable and useable by a person of average strength and skill.

BRIEF DISCLOSURE OF INVENTION

The invention is an apparatus for increasing the flow of blood in a patient, for example a person suffering cardiac arrest. The apparatus comprises a base contoured to seat near a central region of the patient's chest. Also included are a manual actuator and a substantially inelastic belt which is for wrapping around the patient's chest. The invention further comprises a force converter mounted to the base. The force converter is connected to the actuator and has belt connectors for connecting to opposite extremities of the belt. The force converter is for converting a force manually applied to the actuator and directed toward the chest into a chest compressing resultant. The chest compressing resultant is directed through the base toward the chest. The force manually applied to the actuator is converted, in addition to the chest compressing resultant, into belt tightening resultants applied to the belt connectors, and directed tangentially to the chest.

The invention contemplates the converter comprising first and second assemblies. The first assembly has a pair of spaced, parallel arms rigidly connected at handle ends by a first hand-grippable handle. The arms of the first assembly are further rigidly connected at opposite, belt ends by a first strut. The first assembly arms are pivotally mounted to the base at a first assembly fulcrum intermediate the handle and belt ends. The second assembly is substantially similar to the first assembly and both assemblies are pivotally mounted to the base, forming a scissors arrangement. A force applied to the handle ends pivots the scissoring assemblies, which form a pair of levers. The strut ends of the assemblies are levered toward one another, tightening the belt attached to the struts.

It is an objective of the present invention to provide an apparatus having a flexible belt which wraps around the chest of a cardiac arrest patient. The apparatus tightens the belt while depressing the chest, the combination of which raises the intrathoracic pressure, enhancing blood flow.

Figure 1:
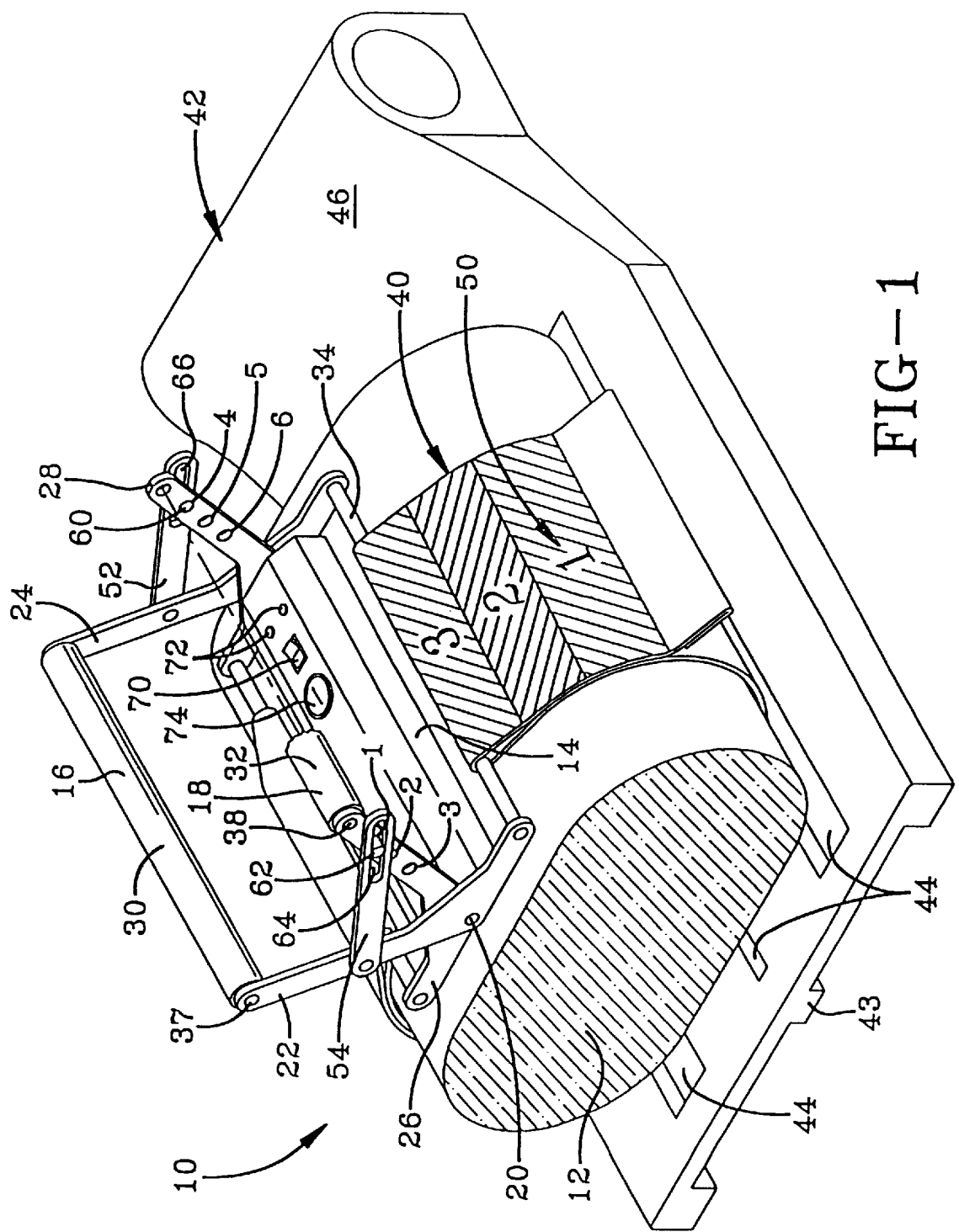
FIG. 1 is a view in perspective illustrating an embodiment of the present invention in an operable position.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose.

DETAILED DESCRIPTION

Figure 16:
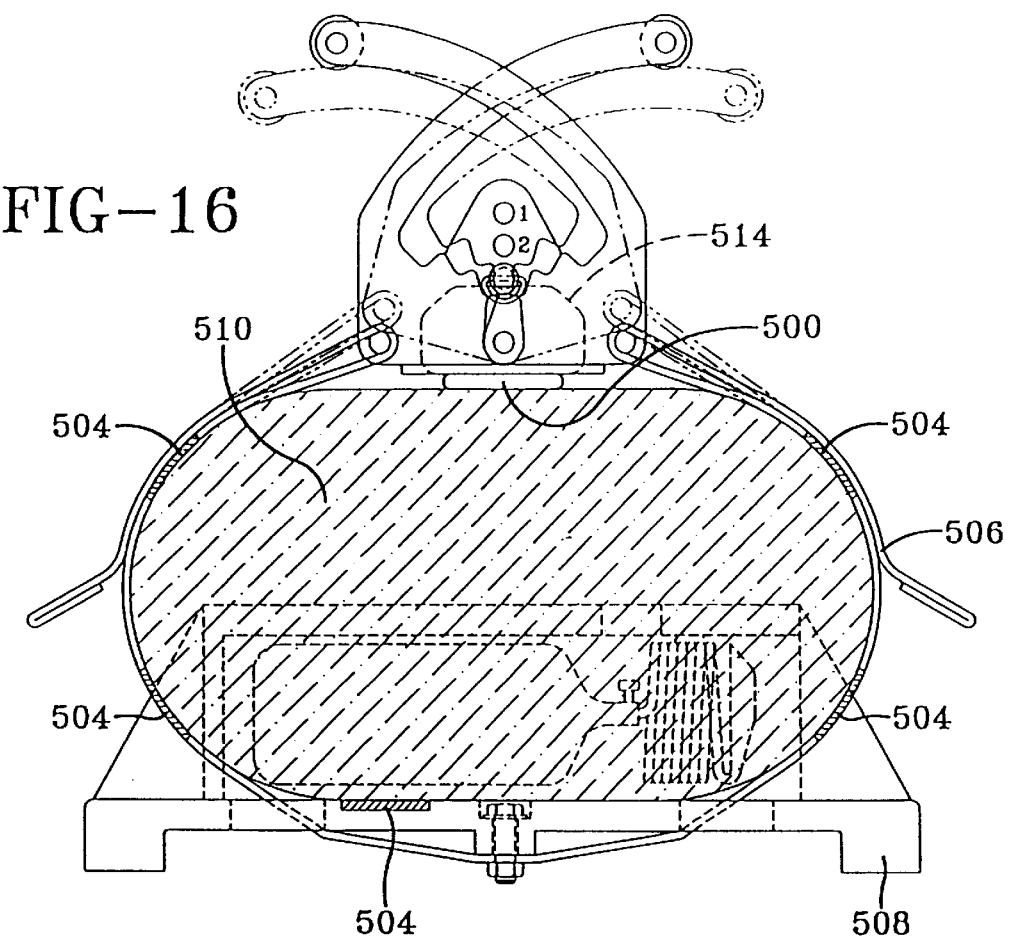
FIG. 16 is a side view in section illustrating a sole of the base.
Figure 17:
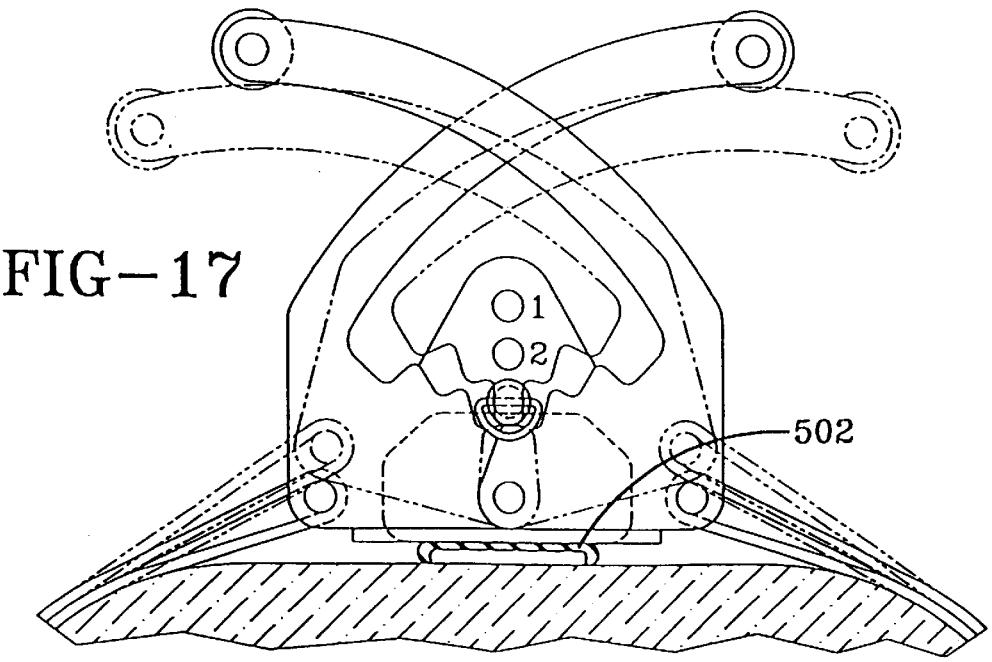
FIG. 17 is a side view in section illustrating another sole of the base.

FIG. 1 shows the apparatus 10, which is an embodiment of the invention, in its operable position on and around a patient's chest 12. The base 14 is a semi-rigid (preferably plastic) plate or block, preferably having a cushioned outer surface contoured to seat against the central region of the patient's chest 12 near the sternum. The sole 92 of the base 14 is seated against the upper surface of the chest 12 and may have an adhesive pad 500 (shown in FIG. 16) or a suction cup 502 (shown in FIG. 17) to adhere to the chest 12 so that pulling on the base 14 will cause the chest 12 to be pulled for decompression.

The base 14 contains a switch 70 and a pair of lights 72. Additionally, the base 14 contains a battery, a battery charge indicator and a sound generator (not visible in FIG. 1) which sound generator emits an audible, periodic signal. The visible and audible signals indicate the frequency to a rescuer of a compressive force he or she is to apply to the apparatus 10. One or more of the audible or visible signals could also prompt the rescuer to apply ventilation. The base 14 also contains a force sensor, such as a strain gauge, and an indicator 74 which indicates the force exerted on the chest 12 to warn the rescuer of potential injury due to excessive force. A limiter could be added to limit some of the force applied to the patient to a specified maximum.

The first arm assembly 16 is made up of a pair of spaced, parallel arms 22 and 24 which are made of high tensile strength, lightweight material such as plastic. The second arm assembly 18 has substantially similar spaced, parallel arms 26 and 28. A pair of rods 37 and 38 rigidly fasten the spaced parallel arms of the assemblies 16 and 18, respectively A pair of manual actuators, which are preferably two cylindrical, hand-grippable handles 30 and 32, are rotatably mounted between the spaced, parallel arms of the first and second arm assemblies 16 and 18, around the rods 37 and 38, respectively. A pair of rod-like, preferably metal struts 34 and 36 (strut 36 not visible in FIG. 1) rigidly mount to the ends of the spaced arms, opposite the handles 30 and 32.

The rigid arm assemblies 16 and 18 pivot relative to one another about the pivot pin 20, which is preferably a stainless steel bolt. The pin 20 extends longitudinally through the base 14 and extends out of each longitudinal end to pivotally attach to each arm 22, 24, 26 and 28.

The arm assemblies 16 and 18 are arranged in a scissor-like configuration. This configuration is designed to convert a small force into a larger force. This is done by the scissor-like configuration having a pair of levers with a common fulcrum, where the fulcrum is located a distance from the center of the levers. A large displacement of the handles 30 and 32 causes a relatively small displacement of the struts 34 and 36. In elementary physics, it is understood that work equals force times distance and the force applied to cause a displacement at one end of a lever should equal the product of force and displacement at the opposite end of the lever. Conservation of work gives $$F_s D_s = F_h D_h \qquad \text{Equation 1}$$

where the subscript s indicates the force or displacement at the struts 34 and 36 and the subscript h indicates the force or displacement at the handles 30 and 32. Solving Equation 1 for the force at the struts 34 and 36 obtains $$F_s = \frac{F_h D_h}{D_s}. \qquad \text{Equation 2}$$

The displacement at the struts 34 and 36 ($D_s$ in Equation 2) will always be smaller than the displacement at the handle ($D_h$ in Equation 2). By separating the displacement part of Equation 2 in parenthesis, the following is obtained:

$$F_s = F_h \left( \frac{D_h}{D_s} \right). \qquad \text{Equation 3}$$

Since the displacement at the struts is smaller than the displacement at the handles, the displacement portion of Equation 3 will be a number greater than 1 which, when multiplied by the force at the handles, will obtain a force at the struts which is greater than the force at the handles. It is this greater force at the struts 34 and 36, effected by the force applied to the handles, which is used to artificially induce or enhance blood flow in a patient.

The pivoting motion of the arm assemblies 16 and 18 is a simple and reliable action which virtually any person can effectuate. Doing so requires a small force, and creates a larger force that is to be applied to a patient's chest 12. The force at the struts 34 and 36 could not be generated by an average person for the time period required to treat a cardiac arrest patient, without the help of a mechanical device.

Two stainless steel stroke limiters 52 and 54 are pivotally mounted to the arms 22 and 24 and slidingly attach to the arms 26 and 28. The limiters 52 and 54 serve the purpose of limiting the relative pivoting displacement of the assemblies 16 and 18 by mechanically restricting their movement. Unlimited displacement between the two assemblies 16 and 18 could result in an excessive compression force on the chest 12 which could injure the patient.

Figure 13:
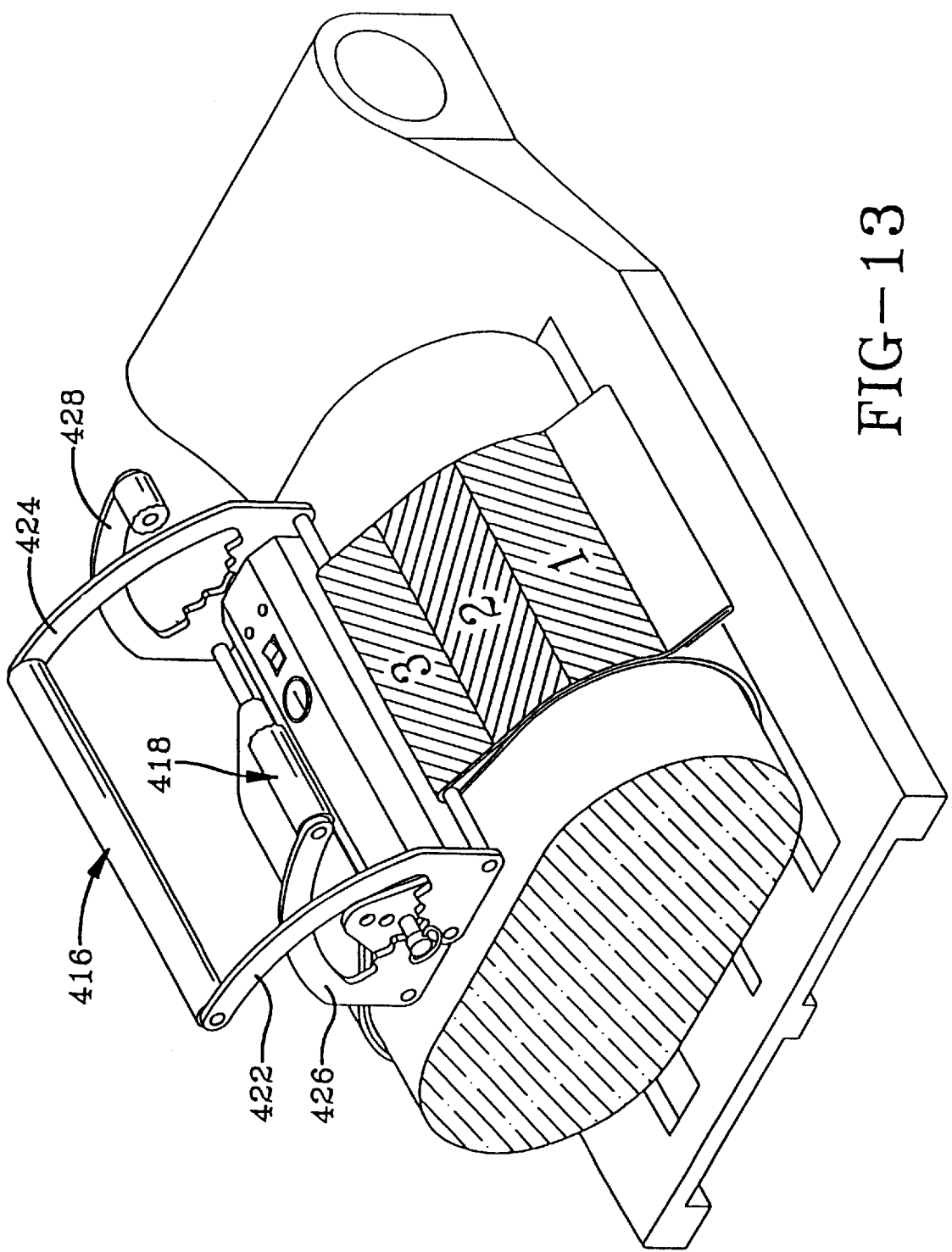
FIG. 13 is a view in perspective illustrating an embodiment of the present invention.

An alternative to the arm assemblies 16 and 18 shown in FIG. 1 is the arm assemblies 416 and 418 shown in FIG. 13. The arm assemblies 416 and 418 are made up of the spaced, parallel arms 422, 424, 426 and 428, respectively. The curved shape of the arms 422–428 making up the arm assemblies 416 and 418has been found to be more advantageous than the angled shape of the arms making up the arm assemblies 16 and 18 shown in FIG. 1. The advantage is found primarily in the means for limiting the relative displacement of the arm assemblies 416 and 418. The preferred means for limiting the relative displacement is shown in greater detail in FIG. 14.

Figure 14:
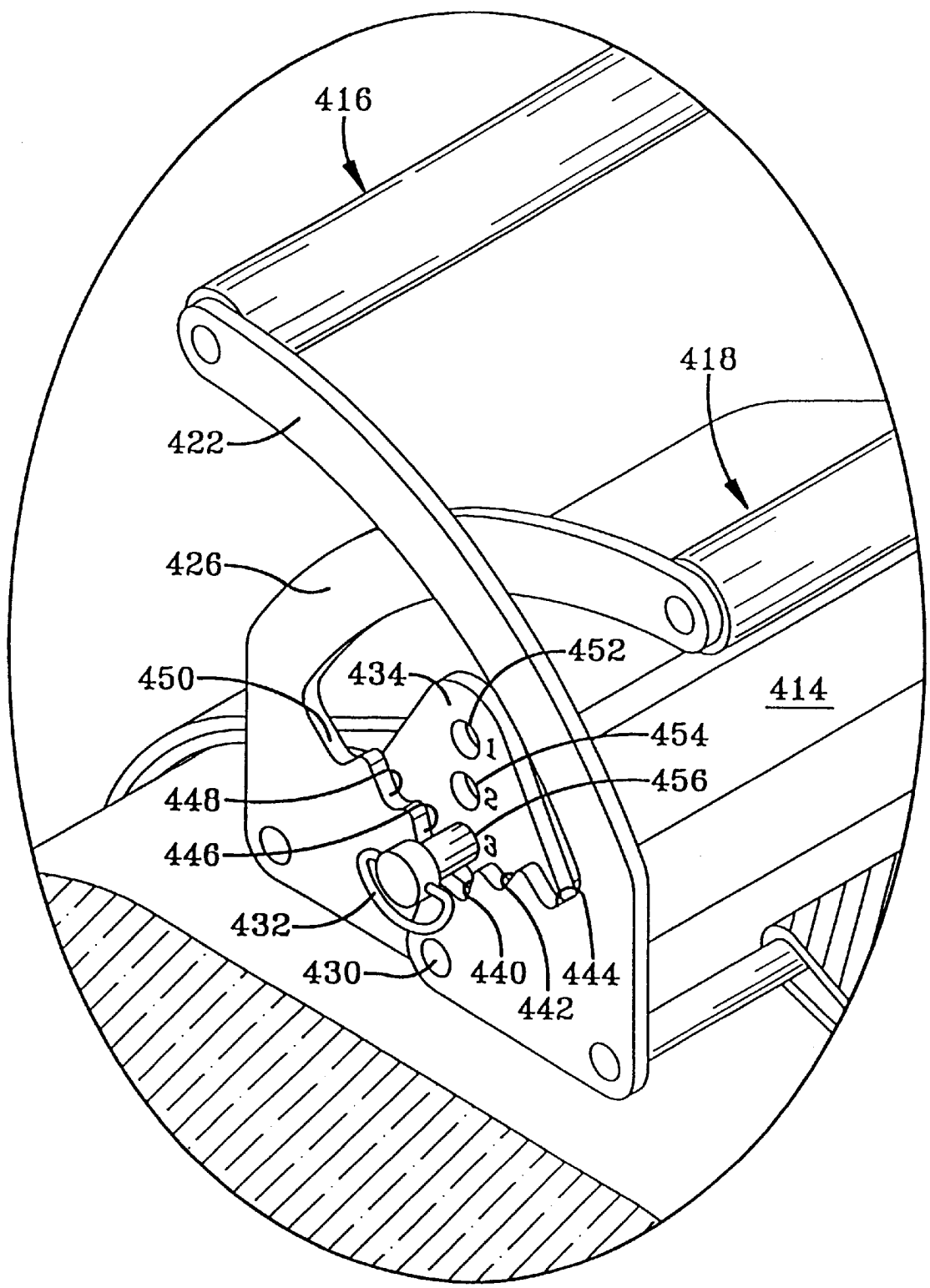
FIG. 14 is an enlarged view in perspective of an embodiment of the present invention.

As the arms 422 and 426, shown in FIG. 14, pivot about the common fulcrum located at the pivot pin 430, they pivot toward the stop pin 432. The stop pin 432 extends through one of three holes formed in an upright 434 which extends rigidly from the base 414. The arm 422 has three shoulders 440, 442, and 444 which face the stop pin 432. The arm 426 has three similar shoulders 446, 448 and 450. In their relaxed position shown in FIG. 14, the arms 422 and 426 have gaps of a predetermined distance between corresponding shoulders. For example, the gap between shoulder 442 and shoulder 448 is a predetermined size when the arms 422 and 426 are in their relaxed position. As the arms 422 and 426 are pivoted toward one another, the gaps between the shoulders decrease in size. In order to insure that the gap between a particular pair of shoulders does not decrease below a specified minimum, the stop pin 432 is placed in one of the three holes 452, 454 or 456 formed in the upright 434. Each hole has an axis which extends into a particular gap. Since the three gaps between the six shoulders 440–450 are of different length, the position of the stop pin 432 in the upright 434 will affect the distance the arms 422 and 426 can travel until two associated shoulders seat against the stop pin 432, restricting further displacement.

Figure 15:
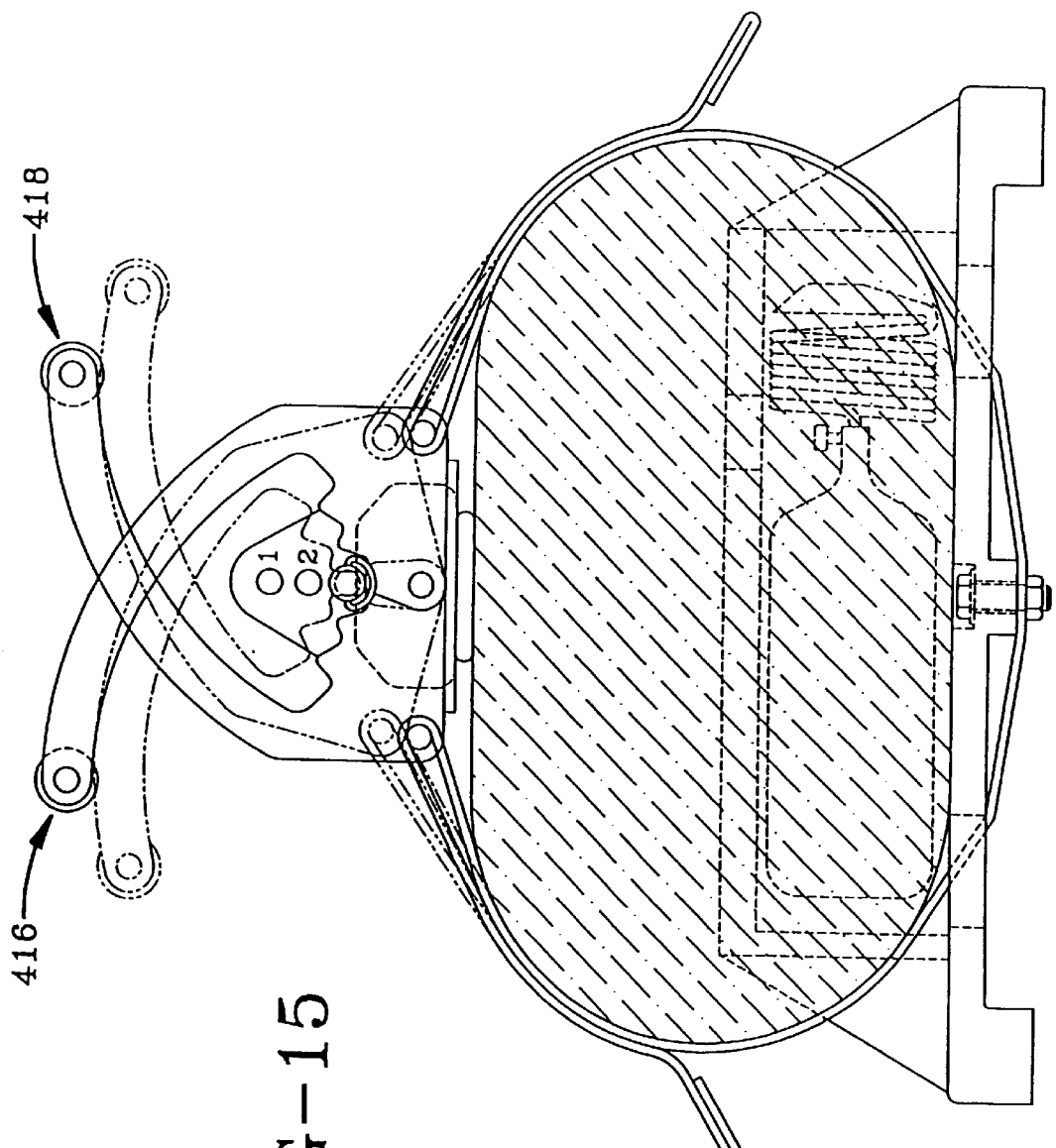
FIG. 15 is a side view in section illustrating the extreme positions of the arm assemblies of the embodiment of the present invention shown in FIG. 13.

For example, FIG. 15 shows the arm assemblies 416 and 418 in their relaxed positions and in phantom in. an extended position. In the extended position, when the stop pin 432 is positioned in the hole 456 of the upright 434, the shoulders 440 and 446 seat against the stop pin 432 to limit the extension of the arm assemblies 416 and 418.

The belt 40, which extends around the front, sides and back of the chest, is substantially inelastic and flexible. A plurality of indicia 50 is imprinted on the exposed surface of the belt 50. The belt 40 attaches to the strut 34 on one side of the chest 12, and extends around a major portion of the circumference of the chest 12 to attach to the other strut 36. When the assemblies 16 and 18 pivot around the pivot pin 20, the belt 40 is tightened by the struts 34 and 36 to which the belt 40 attaches.

Although the belt 40 is described as extending around the front, sides and back of the chest, the belt may be made up of two or more component parts, such as a pair of belts. This pair of belts could extend from attachment to the struts 34 and 36, extending downwardly past the sides of the patient's chest to rigid attachment to a board which spans the width of the back of the chest. Therefore, "a belt wrapped around the chest" can be made up of two or more belt components which extend around portions of the chest circumference in combination with other rigid or flexible components.

Figure 2:
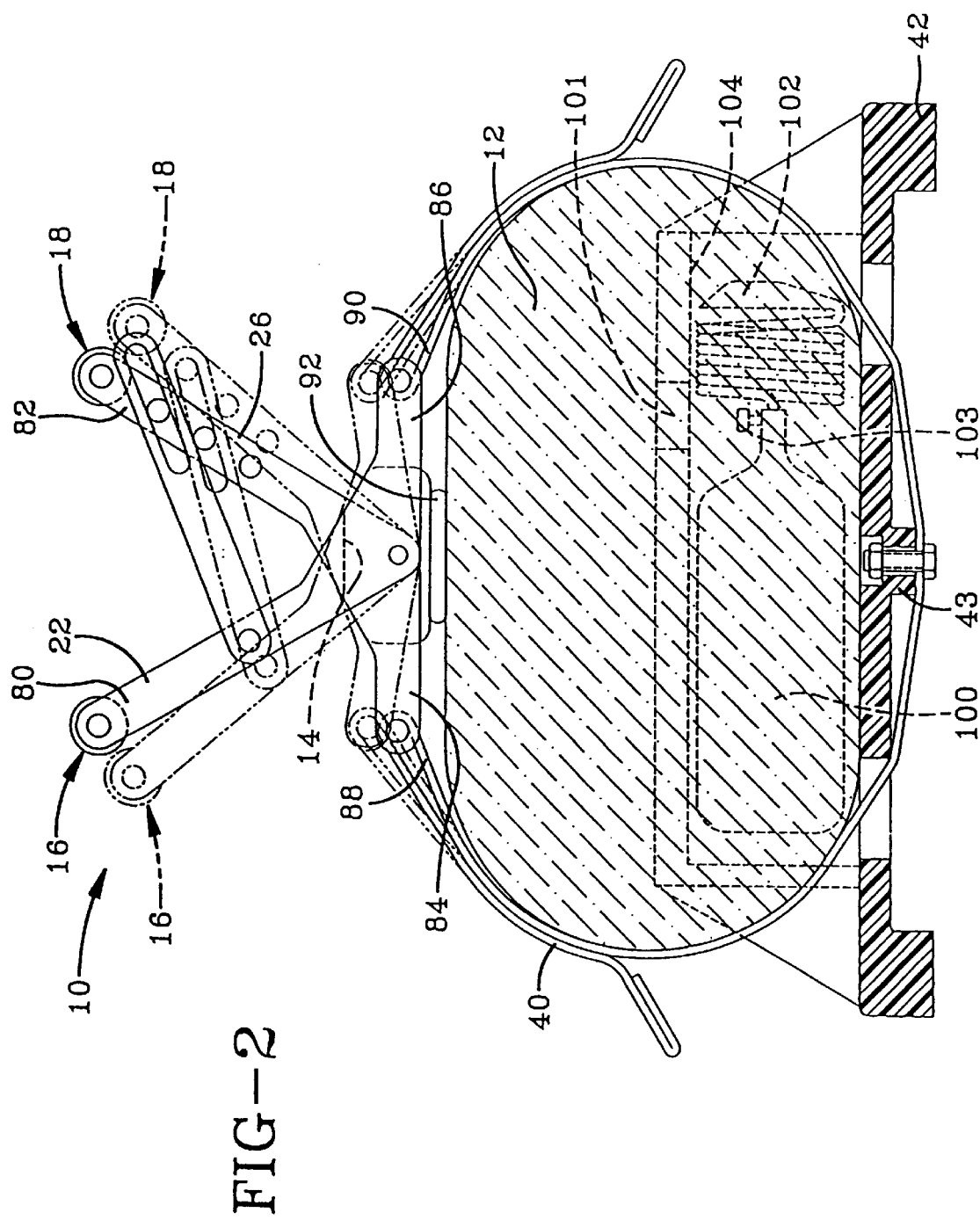
FIG. 2 is a side view in section illustrating the extreme positions of the arm assemblies of the embodiment of the present invention shown in FIG. 1.

The relaxed and mid-actuated positions of the arms of the apparatus 10 are shown in FIG. 2. The first and second assemblies 16 and 18 are shown in their relaxed position and (in phantom) at the mid-point of their actuated position. The assemblies 16 and 18 are biased into the relaxed position by a spring (not shown) which could be a torsion spring extending around pin 20 and connecting to the assemblies 16 and 18. The handle ends 80 and 82 of the arms 22 and 26 pivot along an arcuate path downwardly and away from each other, and the belt ends 84 and 86 of the arms 22 and 26 pivot upwardly and toward one another in an arcuate path subtending the same angle as the handle ends 80 and 82. The belt extremities 88 and 90 (which are the looped ends of the belt 40 which attach to the struts 34 and 36) follow the belt ends 84 and 86 of the arms to an upward and more proximally spaced position. Since the belt 40 is substantially inelastic, its circumference will decrease under the force applied to it by the struts 34 and 36, thereby tightening the belt 40 around the chest 12.

The belt 40 extends through slots 44 formed in a backboard 42 which, when in use, is positioned beneath the chest 12 of the patient. The belt 40 preferably seats against a sliding mechanism 43 which permits sliding of the belt 40 along the length of the chest 12 for positioning of the belt 40 on the chest 12. The backboard 42 is made of a strong, lightweight material such as plastic and is wide enough to span the width of the chests of a large majority of the population. The backboard 42 has a padded, raised portion 46 which elevates the patient's neck above his head for opening the breathing passages, and the backboard 42 preferably has handles 250 and 252 (shown in FIG. 9) for carrying the backboard 42 with or without a patient lying on it. The backboard 42, the attached belt 40 and the assemblies 16 and 18, are all hung on a wall by extending hooks through the handles 250 and 252 or by some other conventional hanging means, and may be hinged near the center for folding during storage.

An oxygen tank 100 and a mask 102 are shown in hidden lines in FIG. 2 as contained within a chamber 104 formed in the backboard 42. A gauge 103, indicating the amount of oxygen in the tank 100, is visible through the port 101. The raised portion 46 of the backboard 42 is suited to the formation of a cylindrical chamber 104 in which the oxygen tank 100 can be easily stored. If needed, the mask 102 can be withdrawn from the chamber 104 and placed over the patient's mouth for enhanced ventilation of the patient's lungs.

The apparatus 10 is operated in the following manner, referring to FIGS. 1 and 2. The victim is placed onto the backboard 42 with his or her chest 12 in the position shown in FIG. 1. The back of the patient's chest 12seats against the surface of the backboard 42 with the patient's neck resting on the raised portion 46 and his head lying on the horizontal surface on which the backboard 42 lies, such as a floor. The base 14 of the apparatus 10 is placed at approximately the center of the patient's chest 12 near the sternum. The belt 40 is then extended upwardly from the backboard 42, between the arms and chest 12, and around opposite sides of the chest 12 to match the relaxed contour of the chest 12. The belt 40 is positioned as high on the chest 12 and as high under the underarms as possible The belt 40 is next extended around the struts 34 and 36, passing first between each strut 34 and 36 and the base 14. The base 14 is more exactly positioned near the center of the chest 12 by matching the indicia 50 on the belt 40 on opposite sides of the base 14. The indicia 50 are alphanumeric characters spaced equally along the length of the belt 40 in a preferably identical arrangement at both ends of the belt 40. The indicia could, of course, be colored bands or other symbols.

Once the belt 40 extends around the struts 34 and 36, the ends of the belt 40 are folded back over onto the portion of the belt 40 contacting the chest 12 and are attached thereto by fasteners. Before fastening, though, the indicia 50 at both struts 34 and 36 must match. For example, the number "3" is shown as the highest number on the belt 40 visible in FIG. 1. In this example, the same number ("3") should be the highest number visible at both struts 34 and 36, which indicates that an equal length of the belt 40 extends from the backboard 42 to the strut 34 as to the strut 36, and therefore that the base 14 is centered on the chest 12.

After fastening the belt 40 to the struts 34 and 36, the stroke limiter pins 60 and 62 extend into the holes 1 and 4 in the arms 26 and 28. Since the number "3" is the highest visible number on the belt 40, the limiter pins 60 and 62 are placed in the distal of the six holes 1–6 in arms 26 and 28. If the number "2" were the highest number visible on the belt 40, the center holes 2 and 5 of the six holes 1–6 on the pivot arms 26 and 28 would be used, since the number "2" would indicate a larger chest circumference than when "3" is the highest visible number. The stroke when the number "2" is the highest visible number is greater than when "3" is the highest visible number This means for a larger chest circumference, the apparatus would be permitted to cause greater displacement of the chest 12.

If the arm assemblies 416 and 418 shown in FIG. 13 are used rather than the arm assemblies 16 and 18 shown in FIG. 1, then the highest number visible on the belt 40 would indicate the positioning of the stop pin 432 in the upright 434. For example, since the number 3 is the highest number visible on the belt 40 in FIG. 1, the stop pin 432 would be placed in the hole 456 which has the indicium "3" next to it. The indicium "3" is visible in FIG. 15, but only the indicia "1" and "2" can be seen in FIGS. 13 and 14.

Once the apparatus 10 is positioned with the belt 40 around the chest 12, the base 14 is centered and the limiters 52 and 54 are in the correct position for the visible indicia 50 on the belt 40, the rescuer depresses the switch 70. This causes the lights 72 to begin emitting a periodic, visible signal and the base 14 to emit a periodic, audible signal in synchronization with the lights 72. The rescuer then grips handles 30 and 32 with his or her hands and, with a downwardly directed force toward the chest 12, pushes the handles 30 and 32, pivoting them about the pivot pin 20, thereby pivoting the arms 22, 24, 26 and 28 through arcuate paths about the pin 20. This pivoting motion causes the struts 34 and 36 at the opposite ends of the arms from the handles 30 and 32 to pivot about the pivot pin 20 in a direction away from the chest 12, but with a smaller displacement than the handles 30 and 32. Pivoting of the struts 34 and 36 draws the ends of the belt 40 closer together, thereby tightening the belt 40 around the chest 12. Since the belt 40 is inelastic, tightening of the belt 40 compresses the chest 12. The arcuate motion of the handles 30 and 32 is limited to a maximum displacement by the stroke limiters 52 and 54, when the pins 60 and 62 contact the ends of the slots 64 and 66. The force on the handles 30 and 32 is released and then exerted again by the rescuer after the handles 30 and 32 have returned to their original positions.

By cyclically depressing with a downwardly directed force, and releasing the handles 30 and 32 (preferably in phase with the lights 72), the rescuer cyclically tightens and loosens the belt 40 around the patient's chest 12. The base 14 concentrates some of the tightening force of the belt in the chest 12 center and prevents pinching of the chest by the scissor-like assemblies 16 and 18. The belt tightening around the chest 12 represents the "thoracic pump" method of artificially inducing blood flow in a cardiac arrest patient by applying a circumferential compressive force to a large area. The large force is from the leverage created by the scissor-like assemblies 16 and 18, and the large area is the circumference of the chest 12.

As the first assembly 16 and the second assembly 18 are forced downwardly toward the chest, the base sole 92 is forced downwardly along a path directed into, and preferably perpendicular to, the chest surface by the downwardly directed force on the handles 30 and 32. Therefore, each depression of the first and second assemblies 16 and 18 results in a downward compression of the center of the chest by the base 14. This is the "cardiac pump" method of inducing blood flow by compressing the heart between the spine and the sternum.

Compressing the organs using the present invention takes advantage of both the "thoracic pump" (belt tightening and loosening) and "cardiac pump" (chest depression by the base 14) methods to convey blood through the blood vessels and, upon release, draw blood back into the organs. Upon each increase in pressure, the blood is compressed out of the organs (and air out of the lungs) and along the vascular system. Upon release, other blood is pulled in. Since the veins have a series of one-way valves, the periodic raising and lowering of thoracic pressure with the present invention creates an artificial blood flow supplying necessary elements to the vital organs, such as the brain, which increases the patient's chances of survival.

The pivoting assemblies 16 and 18 comprise a force converter which converts the downwardly directed chest compressing force applied to the handles 30 and 32 into multiple resultant forces. These resultant forces include a downwardly directed force applied from the base 14 into the chest 12 and two equal tangential forces applied by the struts 34 and 36 to the belt 40. The forces are applied tangentially to the chest 12 since the belt 40 wrapped around the chest 12 and pulled taut must be tangential to the chest 12 surface if it contacts the chest at the chest sides as shown in FIG. 1 The assemblies 16 and 18 comprise the force converter which is a device that converts the force manually applied to the handles 30 and 32, and directed toward the chest 12, into the resultants described above (specifically, a chest compressing resultant and a pair of belt tightening resultants).

A converter for converting the above described applied force into the resultants includes all equivalents to the preferred force converter. A converter need not merely redirect a specific force but could amplify, reduce or signal a device to generate other forces, by the application of a force.

The force necessary to generate sufficient pressure in the chest cavity to create blood flow can be generated by an average person if a device utilizes an applied force correctly. In the position in which a cardiac arrest patient is normally found, a rescuer cannot normally, without leverage, generate a downward force into the patient's chest sufficient to generate the necessary intrathoracic pressure without the risk of injury. The apparatus of the present invention uses the force which an average person can apply and converts the applied force into resultant forces in the directions needed while limiting the maximum displacement of the chest to prevent injury.

Figure 3:
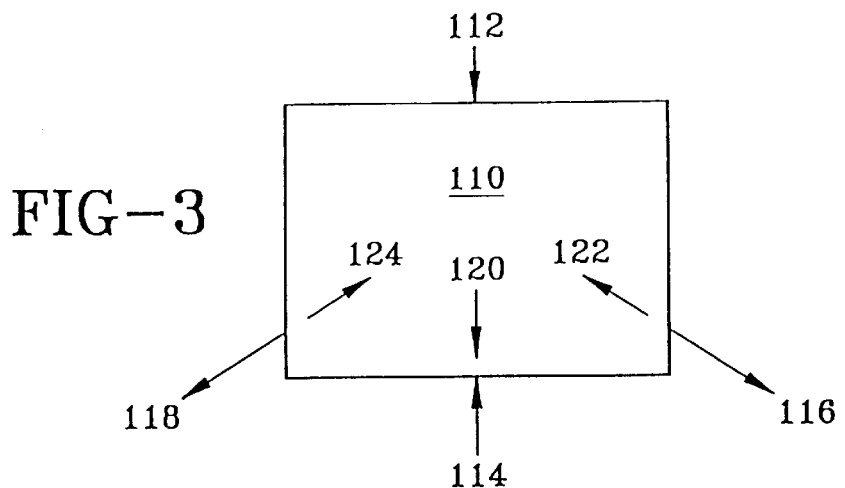
FIG. 3 is a diagrammatic view illustrating a force diagram.

The force converter described above can be considered as a free body shown in FIG. 3 having an applied force 112 directed downwardly onto the converter 110. An opposite force 114 is applied by the chest against the converter 110 as a reaction to the opposite force 112. The tangential forces 116 and 118 are the forces of the belt, extending circumferentially around the chest, pulling on the converter 110. The converter 110 converts the downwardly directed force 112 into resultant forces 120, 122, and 124. The resultant force 120 is directed into the chest along a direction similar to the applied force 112. The resultant forces 122 and 124 apply a tangential tension force to the belt which is tangential to the patient's chest.

The preferred embodiment of the present invention is one device the Applicants have found advantageous for converting the downward force 112 into the three resultant forces 120, 122 and 124. The Applicants know that many apparatuses are equivalent to, and could be substituted for, the preferred apparatus to provide the force conversion described in association with FIG. 3. Although it is impossible to list every mechanical device which one skilled in the art will. know can convert an applied force into the desired resultant forces, some of the many equivalents are described herein. However, this is not an exhaustive list, and other equivalents exist as will become apparent to those skilled in the art.

Figure 4:
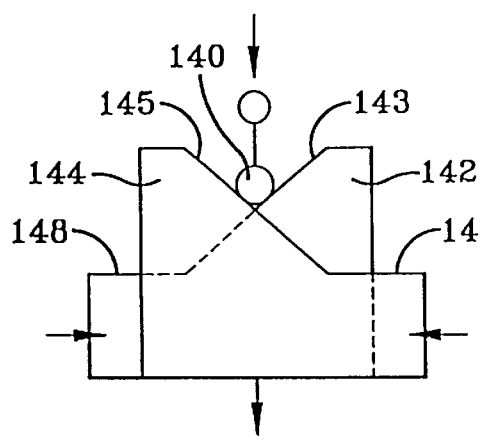
FIG. 4 is a diagrammatic view illustrating an alternative force converter.

FIG. 4 shows a diagrammatic illustration of a cam 140 and a of pair of cam followers 142 and 144. Upon the application of a downward force by the cam 140 onto a pair of inclined surfaces 143 and 145, the follower 142 will slide rightwardly and the follower 144 will slide leftwardly, thereby exerting forces on the belt ends attached thereto, tightening the belt. The cam 140 will slide down the inclined surfaces of followers 142 and 144, and upon reaching the horizontal surfaces 146 and 148, will stop abruptly— exerting a downward force onto the surface beneath the followers 142 and 144, which could be the base of the present invention. The apparatus of FIG. 4 is equivalent to the preferred force converter apparatus.

Figure 5:
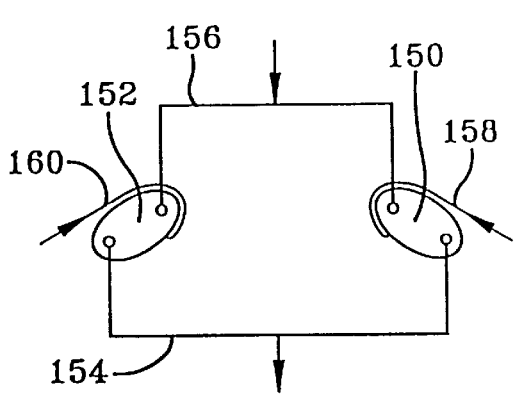
FIG. 5 is a diagrammatic view illustrating an alternative force converter.

FIG. 5 shows a diagrammatic illustration of a first eccentric 150 and a second eccentric 152 pivotally mounted to a base 154. A manual actuator 156 attaches to a second pivot on each eccentric. A pair of belt ends 158 and 160 wrap around the eccentrics 150 and 152, respectively. Upon the application of a downwardly directed force on the actuator 156, the eccentrics 150 and 152 pivot about the pivot points, exerting a force on the belt ends 158 and 160 causing a tightening of the belt. The eccentrics 150 and 152 will, upon a sufficient downwardly directed force on the actuator 156, impact upon the base 154, exerting a downwardly directed force on the base 154 as in the preferred embodiment. The apparatus of FIG. 5 is equivalent to the preferred embodiment.

Figure 6:
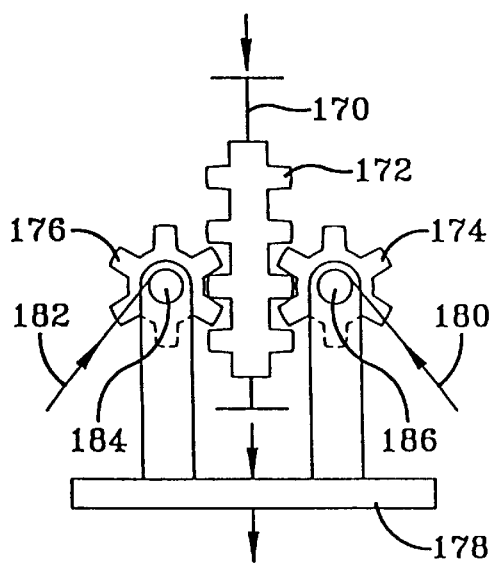
FIG. 6 is a diagrammatic view illustrating an alternative force converter.

FIG. 6 illustrates a diagrammatic illustration of another equivalent to the preferred embodiment including an actuator 170 to which a downwardly directed force is applied. The actuator 170 has a two-sided toothed surface 172 which inter-engages with a pair of gears 174 and 176. Gears 174 and 176 are pivotally mounted to a base 178 and a pair of belt ends 180 and 182 wrap around a pair of drums 184 and 186 at each of the gears 174 and 176. The toothed surface 172, upon a downwardly applied force to the actuator 170, causes the inter-engaging gears 174 and 176 to rotate, thereby applying a force to the ends 180 and 182 of the belt. The actuator 170 impacts the base 178upon being actuated to a certain extremity, thereby exerting a downwardly directed force to the base 178 as in the preferred embodiment.

Figure 11:
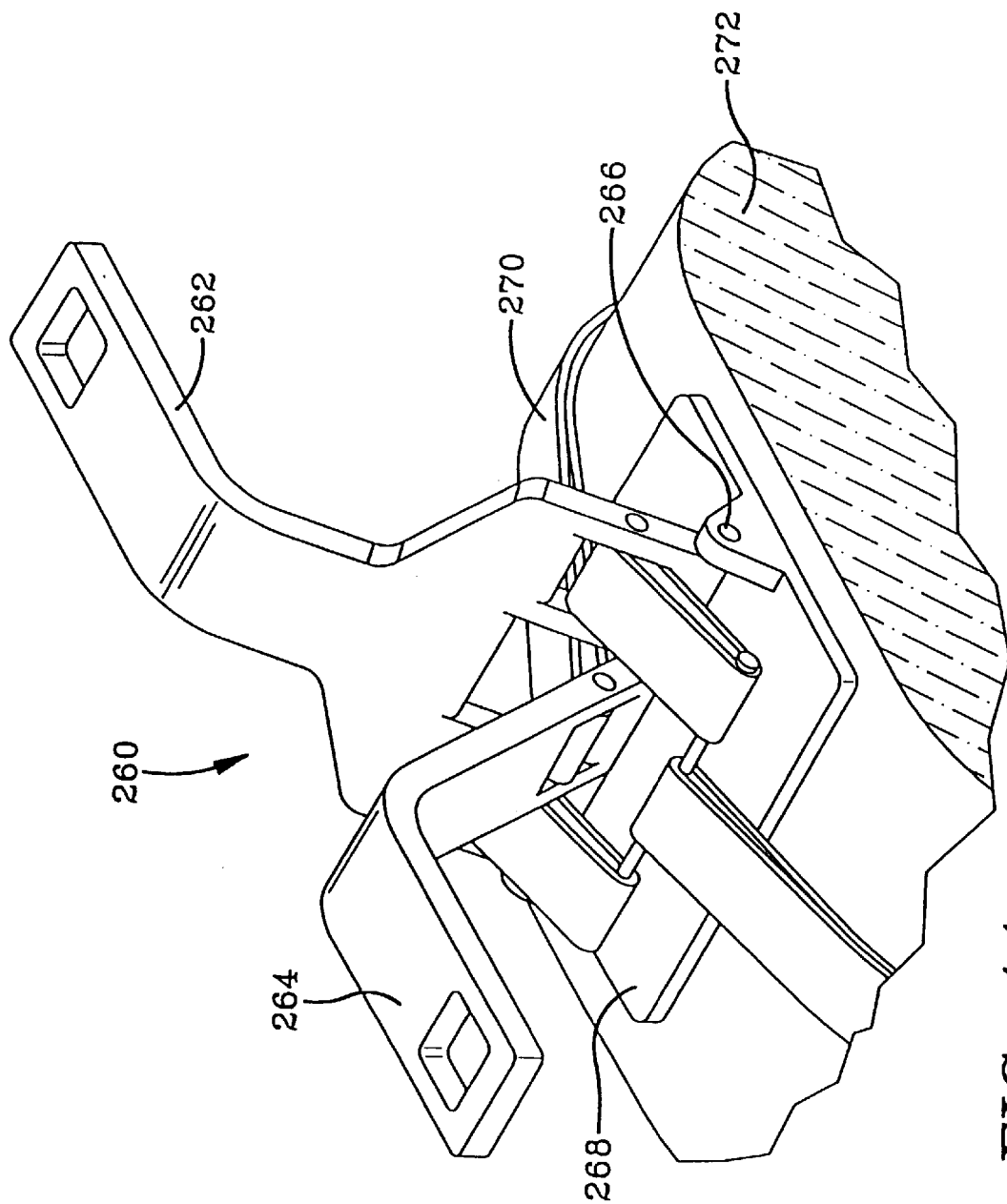
FIG. 11 is a view in perspective illustrating an alternative embodiment of the present invention.

Another alternative, mechanical apparatus 260 which is equivalent to the preferred embodiment is shown in FIG. 11. The apparatus 260 has a pair of pivoting arms 262 and 264 which pivot about a pivot axis 266 on a base 268. A belt 270 attaches at opposite longitudinal ends to the arms 262 and 264. The base 268 is positioned on a patient's chest 272, the belt 270 is extended circumferentially around the chest 272 and attached to the handles 262 and 264. A downwardly directed force is applied to the handles 262 and 264, tightening the belt 270 as the arms 262 and 264 pivot about the pivot pin 266. In addition to the tightening of the belt 270; the base 268 is forced downwardly into the chest 272.

Figure 12:
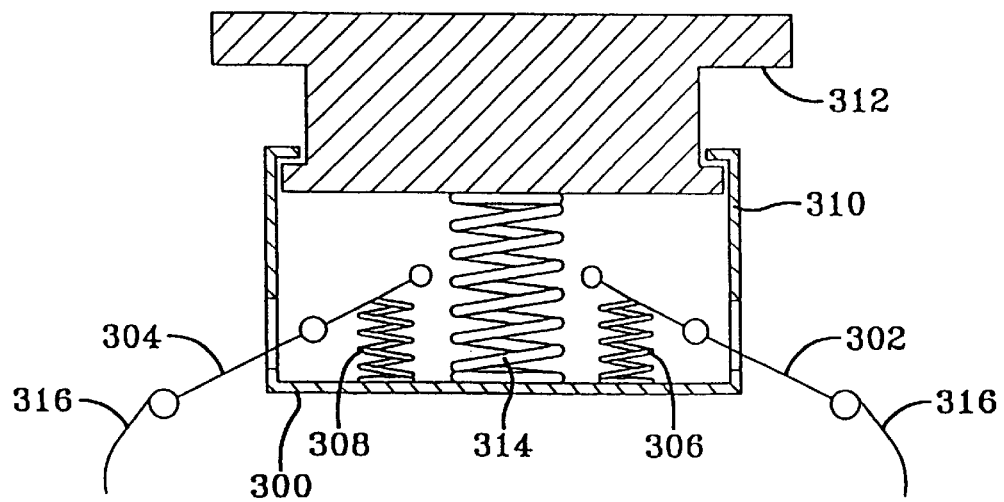
FIG. 12 is a diagrammatic view illustrating an alternative embodiment of the present invention.

FIG. 12 shows a two-chamber device having a base 300 and two pivoting arms 302 and 304. Two springs 306 and 308 keep two arms 302 and 304 biased upwardly within the chamber 310. A plunger 312 is biased away from the chamber 310 by a spring 314. The belt 316 is attached to the arms 302 and 304. Upon downward compression of the plunger 312, the arms 302 and 304 are rotated counterclockwise and clockwise, respectively. This rotation tightens the belt 316 and a patient's chest is compressed with the tightened belt 316 and with the base 300, especially when the plunger 312 reaches the lower limit of the chamber 310.

Many illustrations show equivalent substitute devices for converting an applied force into the desired resultant forces. Most of those described above show purely mechanical equivalents to the preferred embodiment. As a person skilled in the mechanical arts will quickly find, there are many other different substitutes for the preferred embodiment. These devices are equivalent to the preferred embodiment or one of the alternatives described above and shown in the drawings. In addition to purely mechanical alternatives to the preferred embodiment, it is of course possible to combine mechanical, electrical, hydraulic and many other elements to arrive at an equivalent substitute for the preferred embodiment. These combination equivalents are discussed below.

Figure 7:
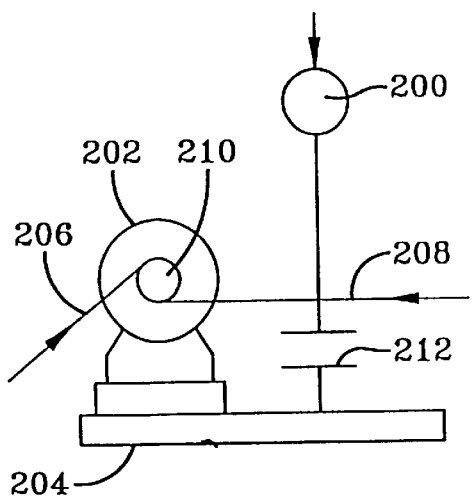
FIG. 7 is a diagrammatic view illustrating an alternative force converter.

In FIG. 7 a mechanical and electrical combination equivalent is shown diagrammatically including an actuator 200 and an electric motor 202 attached to a base 204. The motor 202 has a pair of belt ends 206 and 208 attached to a driveshaft 210. Upon depression of the actuator 200, a pressure-sensitive switch 212 actuates the motor 202, rotating the driveshaft 210 and exerting a linear force on the belt ends 206 and 208. As the force is applied to the actuator 200, this downwardly directed force is transmitted through the base 204 to the patient's chest which lies directly beneath the base 204. The embodiment of FIG. 7 is equivalent to the preferred embodiment.

Figure 8:
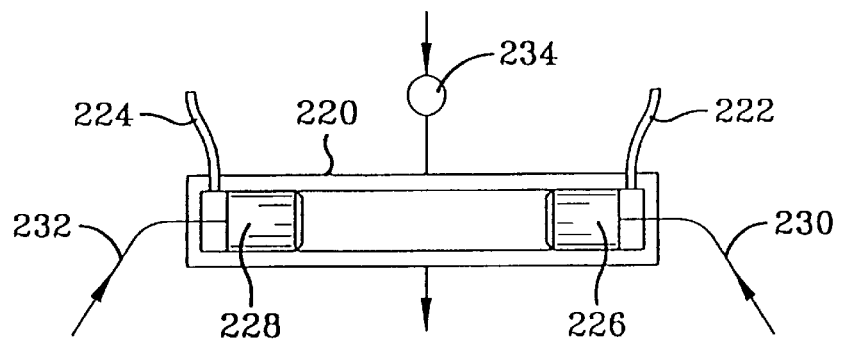
FIG. 8 is a diagrammatic view illustrating an alternative force converter.

FIG. 8 shows still another equivalent to the present invention in a diagrammatic illustration including a hydraulic cylinder 220, fluid lines 222 and 224, and pistons 226 and 228 slidingly mounted within the cylinder 220. The belt ends 230 and 232 are mounted to the pistons 226 and 228. Upon actuation of an actuator 234, hydraulic fluid is forced into the hydraulic cylinder 220 forcing the pistons 226 and 228 toward one another longitudinally, thereby exerting a force on the belt ends 230 and 232. The actuation of the actuator 234 is accomplished by a downwardly directed force which exerts a similar force to a patient's chest lying directly beneath the hydraulic cylinder 220.

The actuator 234 could be attached to a central piston which compresses a fluid within a hydraulic cylinder. Upon actuation of actuator 234, the hydraulic fluid within the cylinder is compressed and is conveyed through the lines 222 and 224 and the pistons 226 and 228 are driven inwardly as described above. This embodiment is also equivalent to the preferred embodiment.

Figure 9:
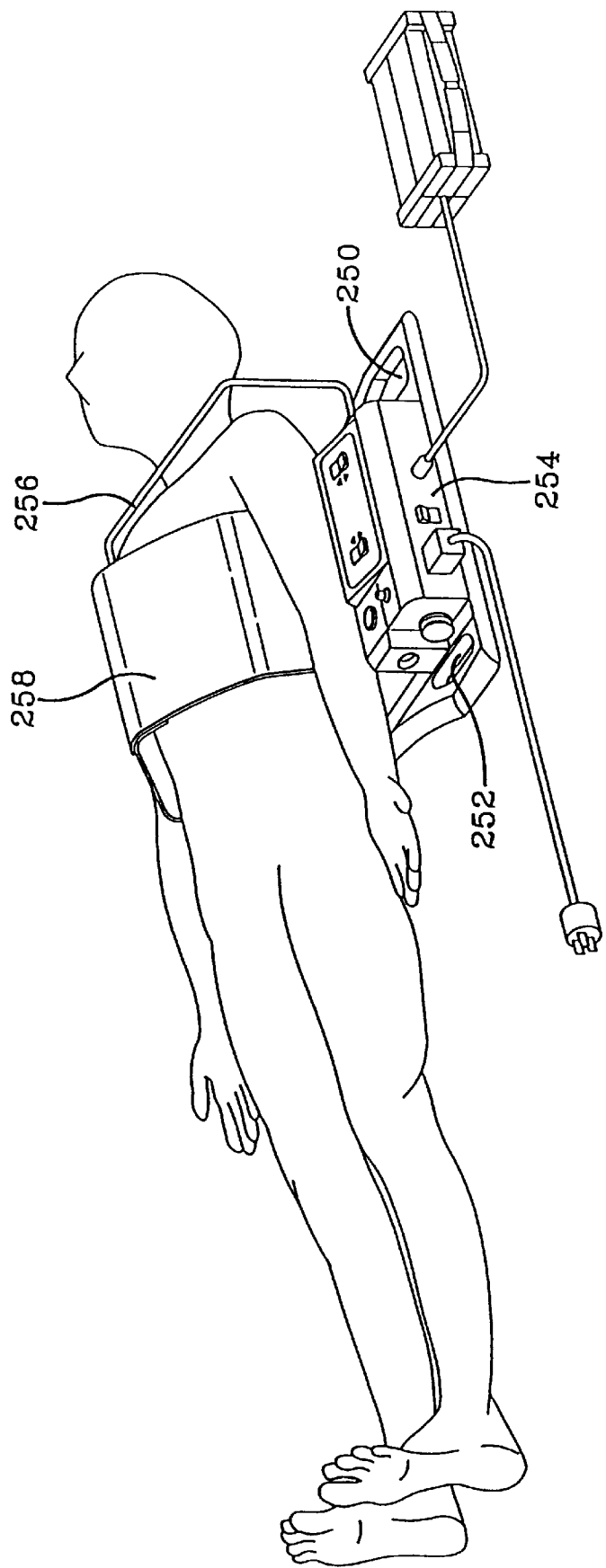
FIG. 9 is a view in perspective illustrating an alternative embodiment of the present invention.

It is possible to attach a power unit, such as a prime mover, to the apparatus 10 which could function as an actuator to apply a lateral force to the arm assemblies 16 and 18 to actuate them automatically and in regular, periodic intervals. As shown in FIG. 9, the power unit 254 has a cable 256 which attaches to a belt 258. The device providing a mechanical force to the belt 258 may be located in the power unit 254 and the cable 256 is then rotatingly driven or longitudinally, reciprocatingly driven to tighten and loosen the belt 258. Alternatively, the actuator which tightens and loosens the belt 258 could be located beneath the belt 258 and the cable 256 would merely convey electrical power or fluid pressure to the actuator. The power unit 254 may use computer controls to time the application of force.

Figure 10:
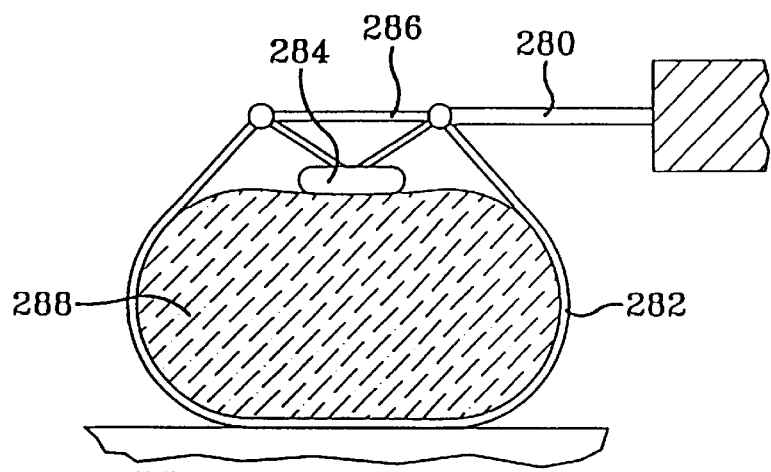
FIG. 10 is an end view in section illustrating a prime mover actuator as part of the present invention.

An example of a power unit 280 applying a force which tightens a belt 282 and depresses a base 284 is shown in the development of another person appearing in FIG. 10. As the rod 286 extends inwardly and outwardly of the power unit 280, the base 284 is displaced upwardly and downwardly, depressing the chest 288 as described with the preferred embodiment. Furthermore, this same mechanical motion of the rod 286 tightens and loosens the belt 282 as with the preferred embodiment.

In order to ensure that the patient's lungs are allowed to expand as much as desired, it may be necessary to include a full-release indicator with the present invention. This indicator should have some means for alerting the rescuer when full release of the tension on the belt has not occurred. This indicator may include a limit switch, a magnet reed relay or contacts on the base 14 against which the arm assemblies 16 and 18 rest in their relaxed position.

Instead of an indicator of full release, a mechanism could be added to the arm assemblies 16 and 18 for preventing the application of force to the handles 30 and 32 until full release (and return to the relaxed position) has occurred. A ratchet mechanism having discreet spacings could be used for this purpose. Additionally, such mechanisms are commonly found on electrical crimping tools for loose terminals.

It is possible to build into the force converter a mechanism for storing and suddenly releasing energy during the application of a downward force. The sudden release would be actuated during the withdrawal of the downward force, applying a short duration, high intensity force to the chest rather than a long duration application of force as with the preferred embodiment.

It is preferred that the apparatus which rests on the top of a patient's chest be as light in weight as possible. The reason for this is that after the patient's chest has been fully compressed, any weight which rests on top of the chest will tend to resist decompression of the chest once the compression force is removed. Reducing this weight minimizes the amount of unwanted compression during release and decompression of the chest The adhesive pad 500m shown in FIG. 16 could contain an electrode which is electrically attached to a voltage generating device as is conventionally known. The adhesive pad 500 could be used in combination with one or more electrodes 504 interposed along the length of the belt 506 or embedded in the backboard 508. These electrodes are used in the conventional manner to induce a current through the chest 510 which is used for defibrillating the patient's heart. Any combination of two or more electrodes can be used to induce a current to defibrillate the heart.

The electrodes 504 can be interposed at multiple positions along the length of the belt 506 or in the backboard 508, but there will preferably be a minimum of one electrode on the base 512 (such as the adhesive pad 500 which functions as an electrode) in addition to at least one other electrode 504. The reason it is desirable to have an electrode at least on the base 512 is that at the furthest extent of compression of the chest 510, the distance between the anterior and posterior outer surfaces of the chest 510 will be at a minimum, and the base 512 will be positioned closer to the heart than at any other point in the whole compression/decompression cycle.

At this point there is a minimum of resistance to the flow of current which gives the greatest current flow through the heart with the least likelihood of injuring the patient's chest 510 tissue.

The electrodes 504 can be positioned not only circumferentially about the chest 510, but can also be positioned at the same circumferential location but at various longitudinal spacings.

It is preferred that a means be adapted to limit the travel of the assemblies 416 and 418 shown in FIG. 13 to only permit the assemblies 416 and 418 to move equal amounts relative to the base. It is undesirable for one assembly to move to one side more than the other assembly, since this causes an imbalance in the application of force, which may result in injury to the patient. The injury arises when a greater force is applied to one edge of the base than the opposite. This can occur if one of the two assemblies 416 and 418 moves a substantially greater distance than the other assembly. One means for limiting their relative motion is a pin in aligned slots in the arms. Another is a gear mechanism connected to both assemblies 416 and 418.

While certain preferred embodiments of the present invention have been disclosed in detail, it is to be understood that various modifications may be adopted without departing from the spirit of the invention or scope of the following claims.

What is claimed is:

1. An apparatus for increasing the flow of blood in a patient, the apparatus comprising:
   (A) a base contoured to seat near a central region of a patient's chest;
   (B) an actuator;
   (C) a substantially inelastic belt configured to wrap around said patient's chest;
   (D) a force converter, mounted on said base, coupled to said actuator, and having belt connectors coupled to opposite extremities of said belt, for converting a force applied to said actuator and directed toward said chest into belt tightening resultants applied to said belt connectors directed substantially tangentially to said chest; and
   (E) safety means, coupled to said converter, for limiting the magnitude of said belt tightening resultants from said force applied to said force converter to a specific magnitude.

2. The apparatus of claim 1 wherein said specific magnitude is a preselected magnitude of a plurality of selectable magnitudes.

3. The apparatus of claim 2 wherein said actuator is a manual actuator and said force is manually applied to said actuator.

4. The apparatus of claim 3 wherein said force converter also converts said force applied to said actuator and directed toward said chest into a chest compressing resultant directed through said base towards the chest.

5. The apparatus of claim 3 wherein said manual actuator comprises first and second hand grippable handles.

6. The apparatus of claim 3 further comprising defibrillating means coupled to said base.

7. The apparatus of claim 6 further comprising first and second spaced electrodes mounted to said apparatus for contacting two spaced outer chest surfaces with said first electrode being mounted to a base outer, chest-contacting surface and said second electrode being mounted to an apparatus chest-contacting surface which is spaced from said first electrode.

8. The apparatus of claim 3 further including a rigid, substantially planar backboard and wherein said belt includes two separate portions with one end of each of said portions attached to said board.

9. The apparatus of claim 8, wherein the other ends of said portions of said belt are attachable to and removable from said force converter.

10. The apparatus of claim 3 further comprising first and second spaced electrodes mounted to said apparatus for contacting two spaced outer chest surfaces with said first electrode being mounted to a base outer, chest-contacting surface and said second electrode being mounted to an apparatus chest-contacting surface which is spaced from said first electrode.

11. A method of CPR treating a patient comprising:
   (A) seating a base of a blood flow increasing apparatus on a patient's chest near a central region of said chest;
   (B) wrapping a belt with first and second opposite extremities around said patient's chest;
   (C) fastening to said apparatus any of said extremities of said belt not already fastened to said apparatus;
   (D) applying a force, directed toward said chest, to an actuator coupled to a converter coupled to said base and said belt;
   (E) converting said force into belt tightening resultants directed substantially tangentially to said chest; and
   (F) limiting the magnitude of said belt tightening resultants from said force applied to said force converter to a specific magnitude.

12. The method of claim 11 further including selecting said specific magnitude of said belt tightening resultants from a plurality of selectable magnitudes.

13. The method of claim 12 further including periodically repeating steps (D) to (F).

14. The method of claim 13 wherein said force is manually applied to said actuator.

15. The method of claim 14 further including converting said force applied to said actuator and directed toward said chest into a chest compressing resultant directed through said base towards the chest.

16. The method of claim 14 wherein applying said force includes manually gripping said first and second hand grippable handles.

17. The method of claim 14 further comprising defibrillating the chest of said patient undergoing CPR.

18. The method of claim 17 further including contacting two spaced outer chest surfaces with a first electrode and a second electrode.

19. The method of claim 14 wherein said belt includes two separate portions and further including attaching one end of each of said portions to a rigid, substantially planar backboard.

20. The method of claim 19 further including attaching the other ends of said portions of said belt to said apparatus.

21. The method of claim 14 further including contacting two spaced outer chest surfaces with a first electrode and a second electrode.

* * * * *